United States Patent [19]
Cote et al.

[11] Patent Number: 5,924,206
[45] Date of Patent: Jul. 20, 1999

[54] REUSABLE DEVICE HANDLE

[75] Inventors: Dana M. Cote, Billerica; Edwin G. Lee, Burlington; Robert W. Pierce, Wrentham, all of Mass.

[73] Assignee: Becton, Dickinson and Company, Franklin Lakes, N.J.

[21] Appl. No.: 08/941,449

[22] Filed: Sep. 30, 1997

[51] Int. Cl.$^6$ .................................................. B26B 5/00
[52] U.S. Cl. ............................. 30/337; 606/167; 606/181
[58] Field of Search ..................... 30/337–339; 81/90.2; 606/167, 181, 182; 279/79–80

[56] References Cited

U.S. PATENT DOCUMENTS

| | | | |
|---|---|---|---|
| 1,577,880 | 3/1926 | Stuart . | |
| 1,940,855 | 12/1933 | Friedman | 30/9 |
| 2,960,769 | 11/1960 | Matwijcow | 30/340 |
| 3,311,976 | 4/1967 | Matwijcow | 30/335 |
| 4,976,724 | 12/1990 | Nieto et al. | 606/182 X |
| 5,342,379 | 8/1994 | Volinsky | 606/167 |
| 5,527,329 | 6/1996 | Gharibian | 606/167 |
| 5,741,291 | 4/1998 | Yoo | 606/181 X |

FOREIGN PATENT DOCUMENTS 8002816  12/1980  WIPO ...................................... 30/338

Primary Examiner—Douglas D. Watts
Attorney, Agent, or Firm—Eric M. Lee; Arthur D. Dawson

[57] ABSTRACT

The reusable device handle of this invention includes a nosepiece, a body, an activation rod, an ejector rod and a biasing mechanism. The nosepiece and the body are generally hollow. The nosepiece is connected to the body. The activation rod and the ejector rod are connected together and are disposed in the nosepiece and the body. The biasing mechanism is disposed in the body and biases the activation rod toward the proximal end of the body so that the proximal portion of the activation rod extends proximally from the proximal end of the body. The distal end of the nosepiece is designed to accept a cartridge therein that holds a blade or some other tool. The cartridge can be removably connected to the nosepiece. By pressing the proximal end of the activation rod, the distal end of the ejector rod contacts the cartridge and ejects the cartridge from the nosepiece.

6 Claims, 8 Drawing Sheets

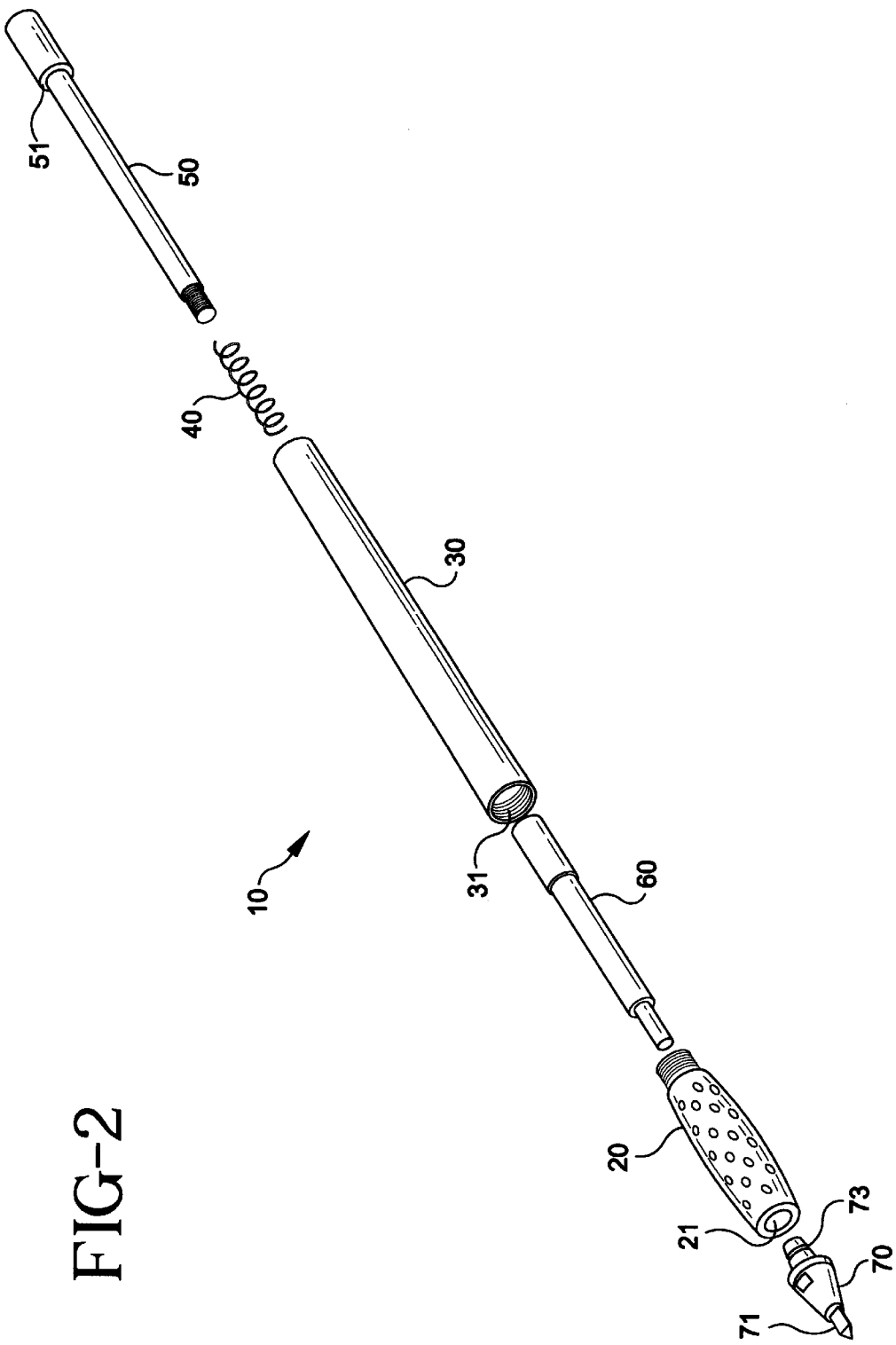

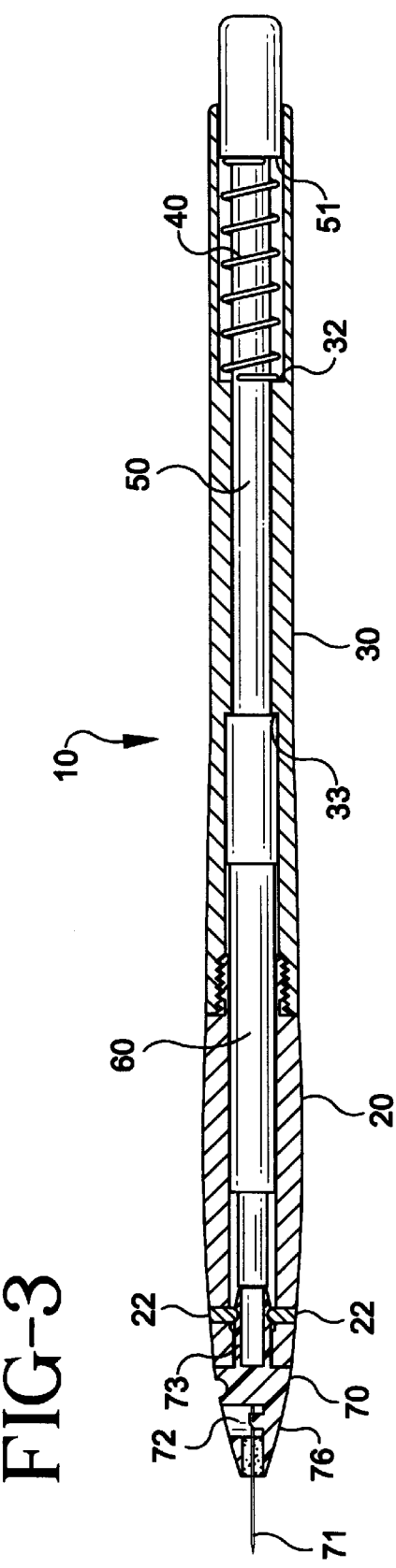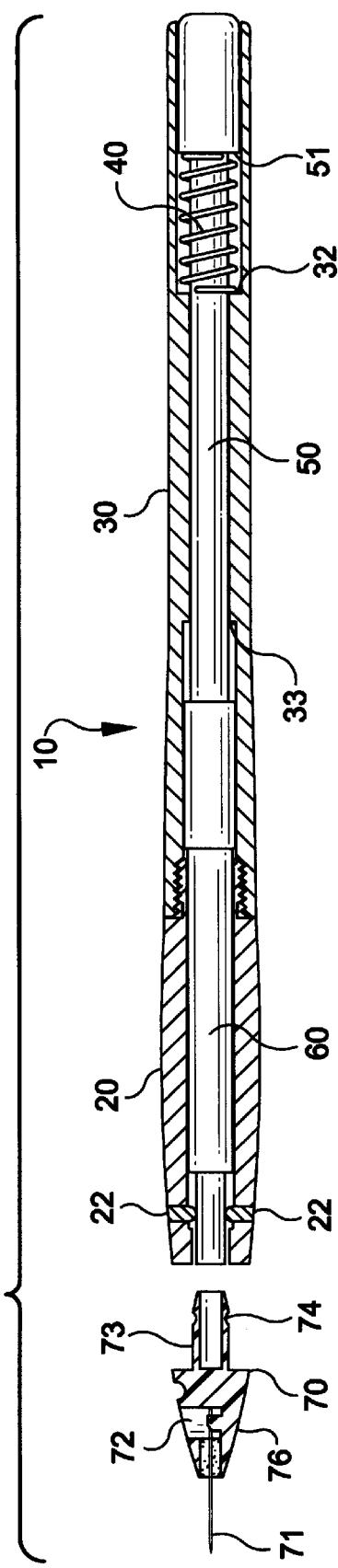

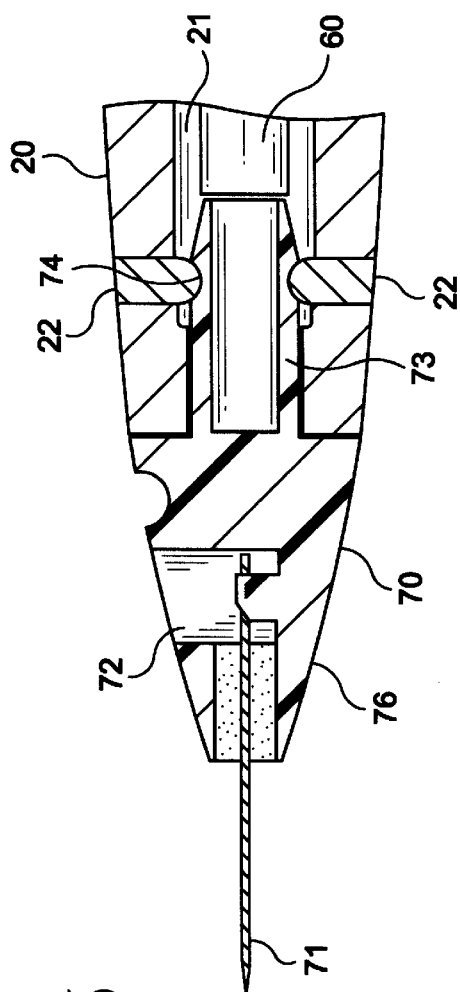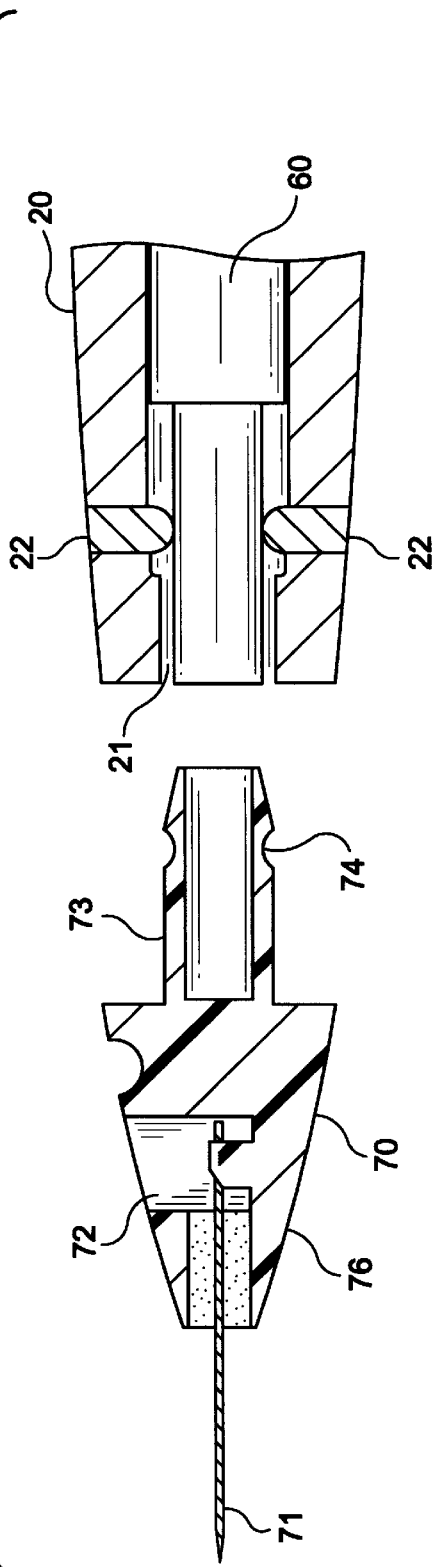

REUSABLE DEVICE HANDLE

BACKGROUND OF THE INVENTION

This invention relates to a reusable handle that may be used in conjunction with various tools or other devices. The device that may be used with the handle may be disposable or may be part of a set of reusable devices particularly adapted for a specific use. This invention is applicable to the medical field, such as surgery, because the handle may be sterilized and is reusable. Even more particularly, this invention is particularly applicable to the field of ophthalmic surgery. This is because a variety of disposable ophthalmic surgical blades having different shapes can be used with the reusable handle.

In various surgical procedures, the physician typically has to make an incision in the patient in order to remove unwanted tissue, repair damaged tissue, or implant a device to improve the patient's well being. In certain cases, all three of these activities or a combination thereof must be done in a single procedure. For example, in cataract surgery, the physician removes the natural lens that has been clouded by a cataract from the patient's eye and replaces it with an artificial lens that will improve the patient's eyesight. In order to perform this procedure, an incision is made in the cornea of the eye by the physician using a scalpel. This provides the physician with access to the patient's lens. The clouded lens is cut loose and removed. There are a number of different procedures that are used to remove a patient's lens that has a cataract. Two of the more common techniques are known as extracapsular surgery and phacoemulsification.

In extracapsular surgery, the physician removes the lens leaving behind the back half of the capsule. In phacoemulsification, the physician fragments the lens by ultrasonic'vibrations. The lens is simultaneously irrigated and aspirated. After the lens is removed, the physician then inserts an artificial lens known as an intra-ocular lens (IOL) into the eye either behind or in front of the iris. Two tiny C-shaped arms connected to the IOL eventually become scarred into the side of the eye and hold the IOL firmly in place.

In another type of ophthalmic procedure known as the Implantable Contact Lens procedure (ICL), the physician makes an incision in the patient's eye and implants a contact lens in the eye in front of the existing lens but behind the iris. This corrects the patient's vision so that he or she can see clearly without the need for external contact lenses or eyeglasses.

Typically a nurse or other surgical assistant manages the devices that are used during surgery. For example, the nurse ensures that the appropriate sterile devices are available in the operating suite for the particular procedure that is to be performed. With respect to scalpels, the nurse often hands the scalpel to the physician in a predetermined orientation so that the physician can grip the scalpel's handle without taking his or her eyes away from the patient. This also minimizes the possibility that the physician will be cut with the blade on the scalpel. After the physician completes the incision the scalpel is handed back to the nurse for proper disposal or sterilization. While the procedure is being performed, this requires the nurse to place the used scalpel on a particular tray that will be removed after the procedure is completed. The devices on the tray are then disposed of or are sterilized for reuse.

If all appropriate protocols are followed, no hospital personnel will be cut by a used scalpel blade. Unfortunately, accidental cuts of hospital personnel do occur. Such accidents may occur for a variety of reasons. For example, because the physician and nurse are concentrating on the patient and the procedure being performed on the patient, they may not pay close attention to the used scalpels. The nurse may put the used scalpels in an inappropriate location or, even if the used scalpels are placed on the proper tray, the blade may be exposed to the operating suite personnel. In these situations, the operating suite personnel may inadvertently come into contact with the blade as they move around the patient during the procedure and be cut or nicked by the exposed blade.

Other hospital personnel may also come into contact with such used blades and be cut or nicked. Usually used blades are disposed of in an appropriate sharps container that allows used needles and blades to be inserted into the container but prevents access by hospital personnel to the sharp end of a needle or the sharp cutting surface of the blade. However, during cleanup of the operating suite, the used blades may be exposed prior to their placement in the appropriate sharps container. And if hospital personnel are not paying close attention to their activities or if the exposed blades are hidden from view because they are buried in a pile of other devices or hospital linen, these hospital personnel may come into contact with the sharp cutting surface of the blade and be cut or nicked.

Cuts and nicks from used blades are uncomfortable and distracting at best. In addition, such cuts and nicks may result in blood or body fluid exposure between the patient and hospital personnel. This may lead to the spread of infectious diseases between the patient and hospital personnel. Concern over this situation has become especially acute in recent years because of such diseases as acquired immuno-deficiency syndrome, i.e. AIDS, and hepatitis. These diseases may be transmitted from an infected person to another person by the transmission of body fluids, typically blood.

In view of the need for a scalpel that can at least minimize the chances of accidental cuts or nicks, numerous scalpels have been designed. These designs typically take the form of a scalpel having a guard that shields the sharp cutting surface of the blade from hospital personnel. The guard in these devices can be moved to a position shielding the blade or exposing the blade for use. Alternatively, the scalpel may be designed to allow the blade to move into or out of the scalpel handle to either shield or expose the sharp cutting surface. Unfortunately, these designs are deficient because they tend to be cumbersome, difficult to use, may cause unwanted shielding or exposure of the blade prior to the need for such shielding or exposure or may require considerable attention by the user to shield or expose the blade. Moreover, such guarded scalpels may provide a false sense of security for hospital personnel. In addition, for reusable devices, even where the guarded surgical scalpel works for its intended purpose, a new blade must be attached to the handle and the used blade must still be removed from the scalpel so a new blade can be attached. This creates an opportunity for hospital personnel to be cut by the used blade while it is being removed from the handle or during transport to a sharps container.

SUMMARY OF THE INVENTION

It is therefore an object of this invention to provide a device that may be used in connection with a sharp blade that minimizes the chances of cuts or nicks during handling.

It is another object of this invention to provide a device that is easy to use.

It is still another object of this invention to provide a device that facilitates the removal of a used blade from the device.

The reusable device handle of this invention includes a nosepiece, a body, an activation rod, an ejector rod and a biasing mechanism. The nosepiece and the body are generally hollow. The nosepiece is connected to the distal end of the body via a detent mechanism that prevents relative rotation between the nosepiece and the body. The activation rod is an elongated generally cylindrical element that extends into the proximal portion of the body. The biasing mechanism is disposed in the body and biases the activation rod toward the proximal end of the body so that the proximal portion of the activation button extends proximally from the proximal end of the body. The ejector rod is disposed in the nosepiece and the distal end of the body. The proximal portion of the ejector rod is connected to the distal portion of the activation rod. The activation rod and the ejector rod must have a total overall length when they are connected that allows the distal end of the ejector rod to be at least flush with the distal end of the nosepiece when the proximal end of the activation rod is flush with the proximal end of the body.

The distal end of the nosepiece is designed to accept a blade cartridge therein. In this configuration with the blade cartridge connected to the nosepiece, a physician may use the reusable device handle of this invention and the blade cartridge just as the physician would use any other standard scalpel. Once the procedure is completed, the physician can press the proximal end of the activation rod. This causes the distal end of the ejector rod to advance distally so as to press against the blade cartridge and eject the blade cartridge from the nosepiece. Thus the physician or other hospital personnel can position the blade cartridge over an appropriate sharps container and eject the blade cartridge directly into a sharps container before handing the reusable device handle over to a nurse. Alternatively, the nurse could easily dispose of the blade cartridge in an appropriate sharps container prior to setting aside the reusable device handle of this invention. The use of a blade cartridge with a reusable device handle can be more economical than using a disposable blade and handle.

Although this invention is described in this document for use as a scalpel in ophthalmic surgery, it is to be understood that this invention is not limited to use with blades. For example, this invention could be used to place a contact lens into a patient's eye in an ICL procedure. Furthermore, this invention is not limited to the field of ophthalmic surgery. This invention also has applicability to other types of surgery in other areas of the body. For example, this invention may be applied in the areas of vascular surgery, implant surgery or any other type of surgery.

The above and other objects and advantages of the invention will be apparent upon consideration of the following detailed description.

BRIEF DESCRIPTION OF THE DRAWINGS

The preferred embodiments are illustrated in the drawings in which like reference numerals refer to like elements and in which:

FIG. 2 is an exploded perspective view of the reusable device handle of this invention including a straight blade cartridge;

FIG. 3 is a cross-sectional view of the reusable device handle of this invention with a straight blade cartridge connected thereto;

FIG. 4 is a cross-sectional view of the reusable device handle of this invention with the straight blade cartridge removed therefrom and the ejector rod and activation rod advanced distally;

FIG. 5 is an enlarged cross-sectional view of the distal portion of the reusable device handle of this invention and a straight blade cartridge connected thereto;

FIG. 6 is an enlarged cross-sectional view of the distal portion of the reusable device handle of this invention with the straight blade cartridge removed therefrom and with the distal end of the ejector rod adjacent to the distal end of the reusable device handle of this invention;

DETAILED DESCRIPTION OF THE INVENTION

Figure 1:
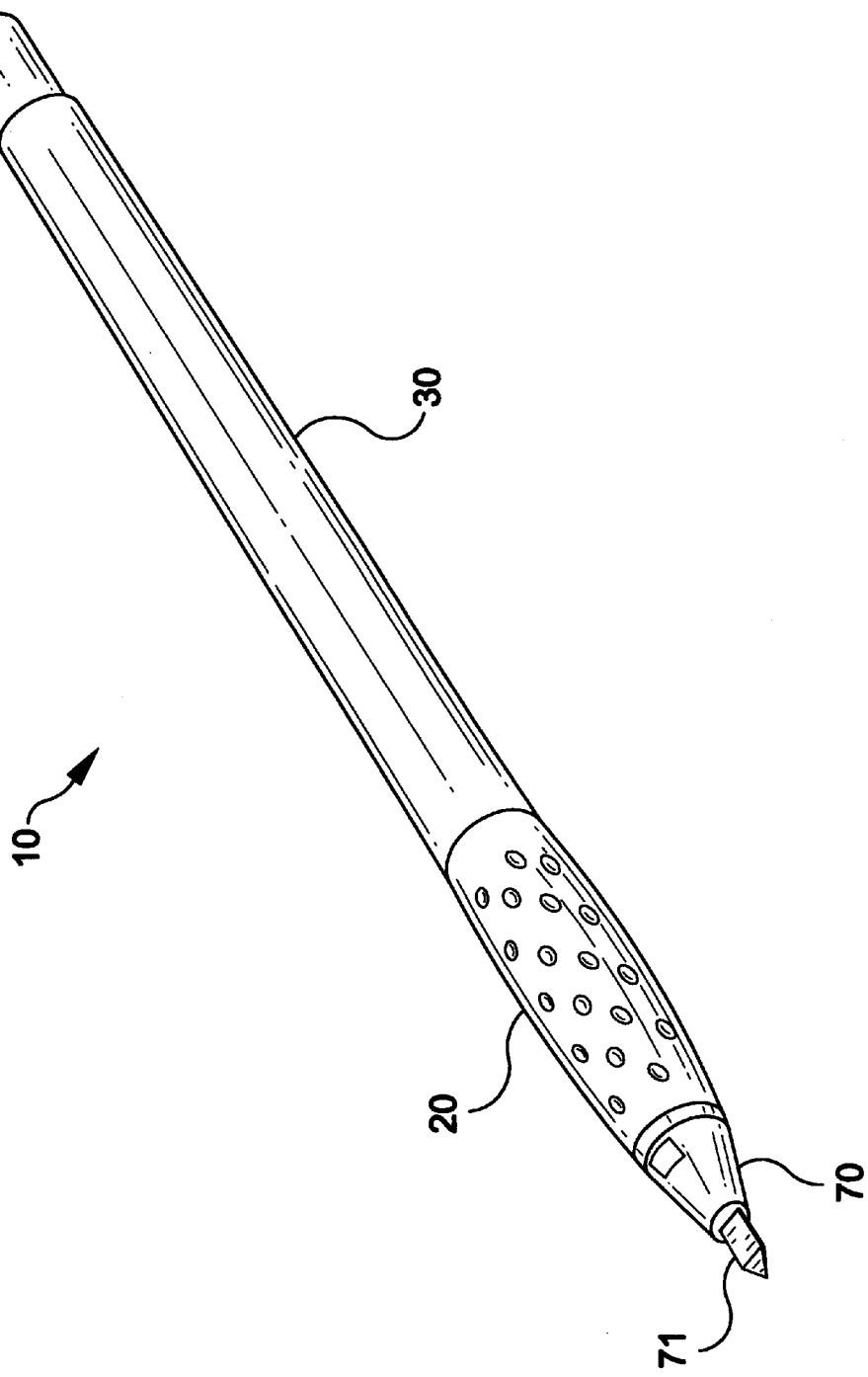
FIG. 1 is a perspective view of the reusable device handle of this invention with a straight blade cartridge connected thereto.

As used herein, the term "proximal" refers to a location on the reusable device handle of this invention closest to the person using the reusable device handle and farthest from the patient in connection with which the reusable device handle is used. Conversely, the term "distal" refers to a location on the reusable device handle of this invention farthest from the person using the reusable device handle and closest to the patient in connection with which the reusable device handle is used.

The reusable device handle 10 of this invention includes a nosepiece 20, a body 30, a biasing mechanism 40, an activation rod 50 and an ejector rod 60. Although reusable device handle 10 is described as having a separate nosepiece 20 and body 30, it is to be understood that a single element could be used that includes an integral body and nosepiece. Similarly, although reusable device handle 10 is described as having a separate activation rod 50 and ejector rod 60, it is to be understood that a single element could be used that includes an integral activation rod and ejector rod. However, it is preferred that reusable device handle 10 include a separate nosepiece 20, body 30, biasing mechanism 40, activation rod 50 and ejector rod 60. This allows reusable device handle 10 to be easily manufactured as well as disassembled into smaller parts that facilitates cleaning and sterilization.

Nosepiece 20 is hollow and is preferably formed from a material that will withstand the rigors of reuse such as titanium, stainless steel or anodized aluminum. All that is required is that the material be tough, durable, easily machinable and able to withstand repeated cleanings and sterilizing cycles in an autoclave. Titanium is the preferred material because of its density, strength and corrosion resistance. Nosepiece 20 defines a nosepiece lumen 21 that is sized to allow the distal end of ejector rod 60 to extend therethrough and to accept the proximal end of a cartridge 70 that holds a blade or some other appropriate tool. Importantly, nosepiece 20 includes a detent mechanism 22 adjacent to the distal end of nosepiece lumen 21. Detent mechanism 22 can take any appropriate form. Detent mechanism 22 could comprise one or more separate pins or balls that are either unbiased or biased by a separate biasing mechanism so that they protrude into nosepiece lumen 21. Alternatively, detent mechanism 22 could be formed by a separate O ring extending into nosepiece lumen 21 or one or more protuberances formed on the inner wall of nosepiece 20 so as to extend into nosepiece lumen 21. Detent mechanism 22 cooperates with a complementary detent configuration 74 formed on the proximal portion of cartridge 70. The configuration of the complementary detent configuration 74 is discussed hereinafter. In this manner, detent mechanism 22 actively engages the proximal portion of cartridge 70 to ensure that cartridge 70 does not easily slip out of nosepiece lumen 21. However, detent mechanism 22 should not engage the proximal portion of cartridge 70 so tightly that excessive force would be required to dislodge cartridge 70 from nosepiece lumen 21. It has been determined that an acceptable force is in the range of between about three to about four pounds.

Alternatively, instead of a separate detent mechanism 22, the distal portion of nosepiece lumen 21 that engages the proximal portion of cartridge 70 can be sized to create an interference fit between the two. In other words, the diameter along the distal portion of nosepiece lumen 21 could be slightly less than the outer diameter along the proximal portion of cartridge 70. This would obviate the need for a separate detent mechanism and make reusable device handle 10 and cartridge 70 easier and cheaper to manufacture.

Body 30 is hollow and is preferably formed from a material that will withstand the rigors of reuse such as titanium, stainless steel or anodized aluminum. All that is required is that the material be tough, durable, easily machinable and able to withstand repeated cleanings and sterilizing cycles in an autoclave. Titanium is the preferred material because of its density, strength and corrosion resistance. The distal end of body 30 can be formed with internal threads in order to connect with the proximal end of nosepiece 20 which can be formed with external threads. However, any other standard mechanical connection mechanism, such as a snap fit or interference fit, can be used to ensure that nosepiece 20 can be connected to and disconnected from body 30. Body 30 defines a body lumen 31 that is sized to accept the proximal end of ejector rod 60 and activation rod 50. Body 30 should also define a pair of internal shoulders 32 and 33. Internal shoulder 32 is adjacent to the proximal end of body lumen 31 to provide a place for the distal end of biasing mechanism 40 to press against and to bias activation rod 50 toward the proximal end of body 30. Internal shoulder 33 is adjacent to the distal end of body lumen 31 to provide a place for the proximal end of ejector rod 60 to rest. The significance of this will be discussed hereinafter.

Biasing mechanism 40 is preferably a compression spring. However, a tension spring could also be used. In addition, some other type of elastic material like an elastic tube that provides the same type of function as a spring could be used instead. All that is required is that biasing mechanism 40 bias activation rod 50 toward the proximal end of body 30. Preferably biasing mechanism 40 extends coaxially around the main portion of activation rod 50 with the proximal end of biasing mechanism 40 engaging an enlarged shoulder 51 formed along a proximal portion of activation rod 50. In this manner, with the distal end of biasing mechanism 40 engaging shoulder 32 in body 30 and the proximal end of biasing mechanism 40 engaging shoulder 51 of activation rod 50, biasing mechanism 40 biases activation rod 50 toward the proximal end of body 30. This bias should ensure that the proximal end of activation rod 50 extends proximally from the proximal end of body 30.

Activation rod 50 has a generally cylindrical cross section and is sized to fit within body lumen 31. Activation rod 50 is preferably formed from a material that will withstand the rigors of reuse such as titanium, stainless steel or anodized aluminum. All that is required is that the material be tough, durable, easily machinable and able to withstand repeated cleanings and sterilizing cycles in an autoclave. Titanium is the preferred material because of its density, strength and corrosion resistance. As discussed above, activation rod 50 is formed with an enlarged diameter proximal portion so that a shoulder 51 is defined between the enlarged diameter portion and the smaller diameter portion. Preferably, only the enlarged diameter portion of activation rod 50 should extend proximally from the proximal end of body 30. The distal end of activation rod 50 is formed with external threads so that activation rod 50 can be connected with ejector rod 60 which preferably has its proximal end formed with internal threads. Alternatively, the distal end of activation rod 50 could be formed with some other standard mechanical connection mechanism so that activation rod 50 could be easily connected to and disconnected from ejector rod 60. For example, the proximal end of ejector rod 60 could be formed with a male portion and the distal end of the activation rod 50 could be formed with a female portion, or vice versa, so that the proximal end of ejector rod 60 and the distal end of activation rod 50 could be connected together, and disconnected, by a snap fit or interference fit.

Ejector rod 60 has a generally cylindrical cross section and is sized to fit within nosepiece lumen 21 and the distal portion of body lumen 31. Ejector rod 60 is preferably formed from a material that will withstand the rigors of reuse such as titanium, stainless steel or anodized aluminum. All that is required is that the material be tough, durable, easily machinable and able to withstand repeated cleanings and sterilizing cycles in an autoclave. Titanium is the preferred material because of its density, strength and corrosion resistance. As discussed above, the proximal end of ejector rod 60 is formed with internal threads or some other connection means so that it can be easily connected to and disconnected from activation rod 50. The proximal end of ejector rod 60 should have a larger diameter than the distal end of activation rod 50. In this manner, the proximal end of ejector rod 60 engages internal shoulder 33 when activation rod 50 is biased toward the proximal end of body 30. This ensures that activation rod 50 and ejector rod 60 are maintained within reusable device handle 10 and are not forced out of the proximal end of body 30 under the force of biasing mechanism 40. Alternatively, if an integral activation rod and ejector rod are used, a portion of the integral activation rod and ejector rod should be formed with a flange to abut internal shoulder 33 and prevent integral activation rod and ejector rod from being removed proximally from the proximal end of body 30.

Although cartridge 70 is described herein as including a surgical blade, it is to be understood that some other appropriate tool could be affixed to cartridge 70. Cartridge 70 can be either straight or angled, i.e. cartridge 70 could be formed with a proximal portion having an axis that is at an angle to the axis of the distal portion. However in both configurations, cartridge 70 has the same basic features. Cartridge 70 comprises a blade 71 and an interface 72. Interface 72 is formed from a tough durable polymeric material such as polycarbonate although other materials could be used. All that is important is that interface 72 be tough and durable and inexpensive so that it can be discarded with blade 71 after a single use. The proximal portion of interface 72 defines a male portion 73. Detent mechanism 74 is formed in the outer periphery of male portion 73.

Figure 7:
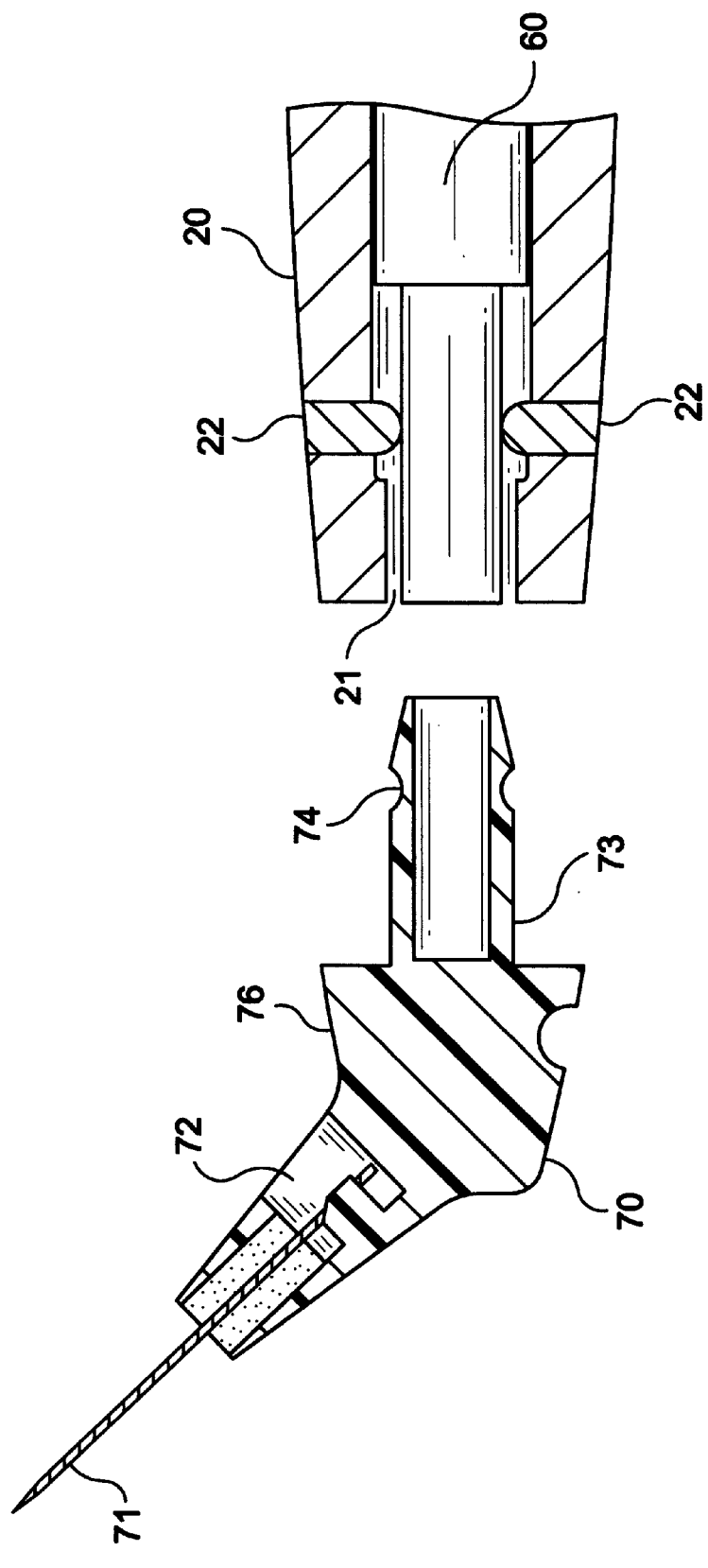
FIG. 7 is an enlarged cross-sectional view of an angled blade cartridge that may be used in connection with the reusable device handle of this invention and the distal portion of the reusable device handle of this invention with the distal end of the ejector rod adjacent to the distal end of the reusable device handle of this invention.
Figure 8:
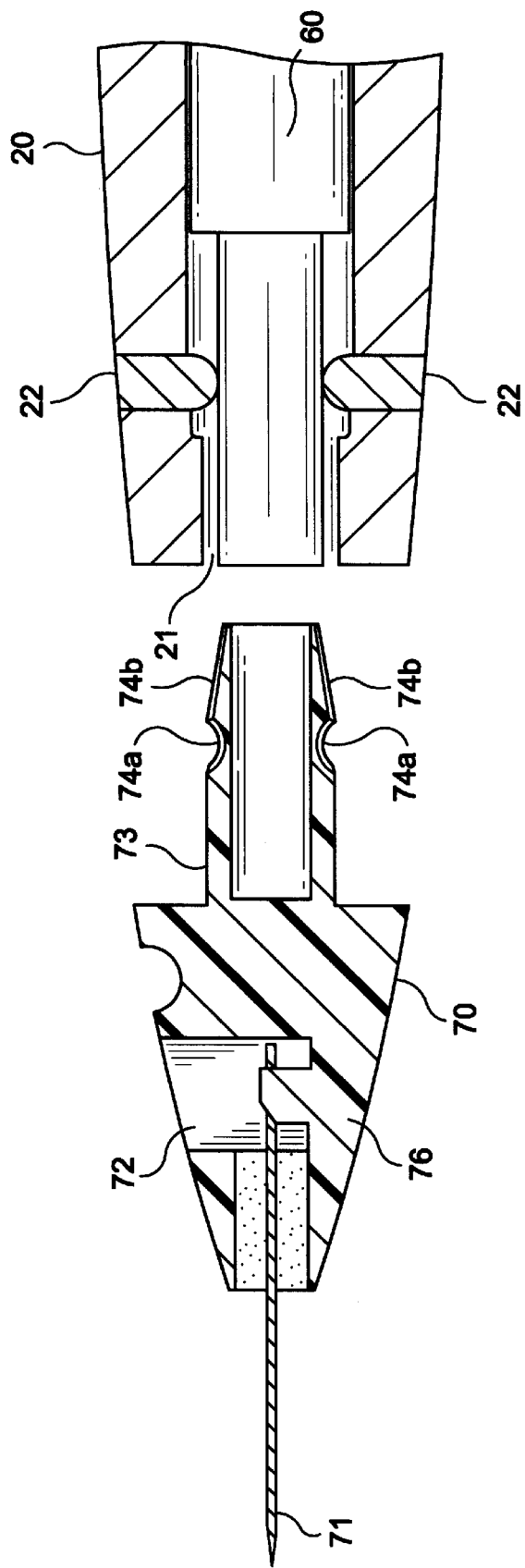
FIG. 8 is an enlarged cross-sectional view of the distal portion of the reusable device handle of this invention with the straight blade cartridge removed therefrom similar to the view of FIG. 6 but showing another embodiment of the proximal portion of the straight blade cartridge.
Figure 9:
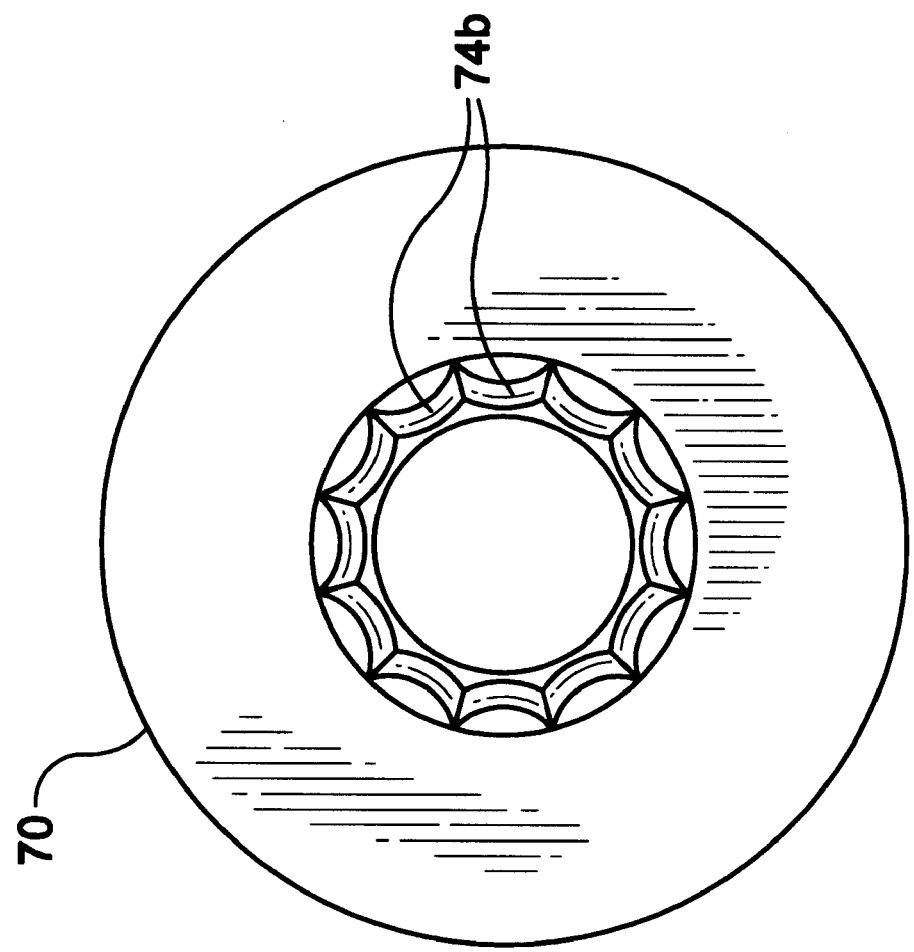
FIG. 9 is a proximal end elevation view of the straight blade cartridge of FIG. 8.
Figure 10:
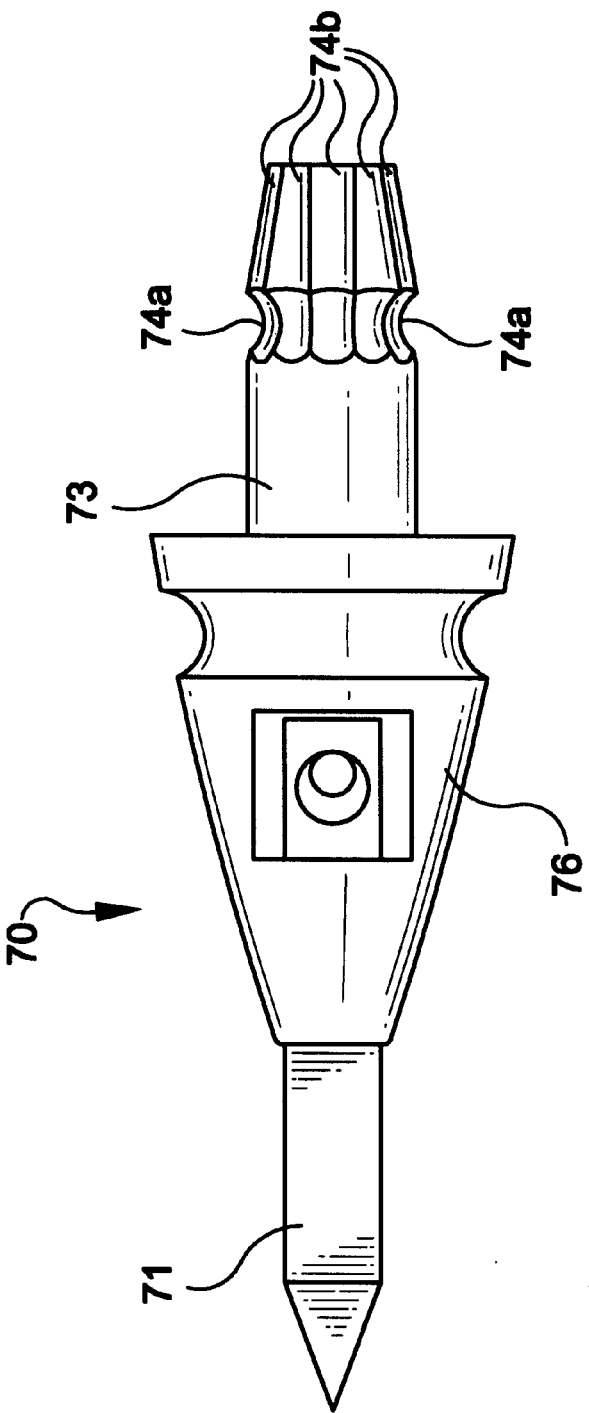
FIG. 10 is a top plan view of the straight blade cartridge of FIG. 8.

Detent mechanism 74 should be complementary to detent mechanism 22 formed in nosepiece 20. Thus detent mechanism 74 could take the form of a cut out or an annular groove so that detent mechanism 22 can be engaged therewith when male portion 73 is fitted into the distal portion of nosepiece lumen 21. Preferably, detent mechanism 74 takes the form of a plurality of divots 74a extending about the circumference of male portion 73. See FIGS. 8–10. Each of the divots 74a is aligned with a track 74b that extends from the proximal end of male portion 73 to the appropriate divot 74a. Each track 74b facilitates longitudinal movement of detent mechanism 22 along male portion 73 during insertion of male portion 73 into the distal portion of nosepiece lumen 21 until detent mechanism 22 seats in an appropriate divot 74a. Once detent mechanism 22 is seated in appropriate divots 74a, relative rotation between nosepiece 20 and cartridge 70 is minimized. In addition, by having a plurality of divots 74a and tracks 74b located about the circumference of male portion 73 the clinician inserting cartridge 70 into nosepiece 20 can easily align detent mechanism 22 with detent mechanism 74. Although divots 74a and tracks 74b extend around the circumference of male portion 73, any lesser number of divots 74a and tracks 74b could be used. Alternatively, as discussed above, male portion 73 could be formed with an outer diameter that is slightly greater than the inner diameter of nosepiece lumen 21 so as to create an interference fit therebetween.

Where cartridge 70 is angled, the axis of male portion 73 is at an angle to the axis of the main body portion 76 of interface 72. See FIG. 7. The angle that is used depends on the procedure to be performed. The angle is designed so that the physician can easily access the desired site without interference from other anatomical structures.

Blade 71 can be secured to interface 72 by any standard connection mechanism. For example, a snap fit, or a press fit could be used. Alternatively, blade 71 could be secured to interface 72 by other bonding means such as by a chemical adhesive.

To use reusable device handle 10 as a scalpel, the distal end of nosepiece lumen 21 is axially aligned with male portion 73 of cartridge 70 that holds a blade and advanced so that male portion 73 of cartridge 70 is securely placed in the distal portion of nosepiece lumen 21 and detent mechanism 22 is fully engaged with detent mechanism 74. A physician may then use reusable device handle 10 and cartridge 70 just like any other standard scalpel. After the procedure is performed, the physician or other user of reusable device handle 10 simply locates cartridge 70 over an appropriate sharps container and depresses the proximal end of activation rod 50. This causes the distal end of ejector rod 60 to engage the proximal end of male portion 73. Continued pressure on the proximal end of activation rod 50 overcomes the resistive force of engaged detent mechanisms 22 and 74. As a result, ejector rod 60 pushes cartridge 70 out of nosepiece 20 and into the sharps container.

Thus it is seen that a reusable device handle is provided that minimizes the chances of cuts or nicks occurring to personnel handling the device when a blade is used in connection with the device, that is easy to use and that facilitates the removal of a used blade from the device.

We claim:

1. A reusable device handle, comprising:
a generally hollow body portion having a proximal and a distal end and defining a body portion lumen therein; a generally hollow nosepiece having a proximal end and a distal end and defining a nosepiece lumen therein wherein the nosepiece is removably connected to the body portion wherein the nosepiece lumen further defines a first detent mechanism;
an activation rod having a proximal end and a distal end and being movably disposed in the body portion,
a biasing mechanism having a proximal end and a distal end and being disposed in the body portion and engaging the activation rod so as to bias the activation rod toward the proximal end of the body portion;
an ejector rod having a proximal end and a distal end disposed in the nosepiece lumen and a distal portion of the body portion lumen and wherein the ejector rod is removably connected to the activation rod.

2. The reusable device handle of claim 1 further comprising a cartridge having a main body portion with a first axis and a proximal male portion with a second axis disposed in a distal portion of the nosepiece lumen.

3. The reusable device handle of claim 2 wherein the first axis of the main body portion is at an angle to the axis of the proximal male portion.

4. The reusable device handle of claim 1 further comprising a cartridge having a main body portion with a first axis and a proximal male portion with a second axis disposed in a distal portion of the nosepiece lumen.

5. The reusable device handle of claim 4 wherein the proximal male portion defines a second detent mechanism complementary to the first detent mechanism.

6. The reusable device handle of claim 5 wherein the first axis of the main body portion is at an angle to the second axis of the proximal male portion.

* * * * *